US010555951B2

(12) United States Patent
Benhadji et al.

(10) Patent No.: US 10,555,951 B2
(45) Date of Patent: Feb. 11, 2020

(54) TARGETED TREATMENT OF LEIOMYOSARCOMA

(71) Applicant: Eli Lilly and Company, Indianapolis, IN (US)

(72) Inventors: Karim A. Benhadji, Green Village, NJ (US); Christophe Massard, Paris (FR); Jean-Charles Soria, Paris (FR)

(73) Assignee: ELI LILLY AND COMPANY, Indianapolis, IN (US)

( * ) Notice: Subject to any disclaimer, the term of this patent is extended or adjusted under 35 U.S.C. 154(b) by 49 days.

(21) Appl. No.: 15/560,676

(22) PCT Filed: Apr. 6, 2016

(86) PCT No.: PCT/US2016/026119
§ 371 (c)(1),
(2) Date: Sep. 22, 2017

(87) PCT Pub. No.: WO2016/168014
PCT Pub. Date: Oct. 20, 2016

(65) Prior Publication Data
US 2018/0104254 A1 Apr. 19, 2018

Related U.S. Application Data

(60) Provisional application No. 62/147,104, filed on Apr. 14, 2015.

(51) Int. Cl.
*A61K 31/55* (2006.01)
*A61P 35/00* (2006.01)

(52) U.S. Cl.
CPC .............. *A61K 31/55* (2013.01); *A61P 35/00* (2018.01)

(58) Field of Classification Search
CPC ................................ A61K 31/55; A61P 35/00
See application file for complete search history.

(56) References Cited

U.S. PATENT DOCUMENTS

| 8,569,286 B2 | 10/2013 | Hipskind | |
|---|---|---|---|
| 2005/0187179 A1* | 8/2005 | Miele ................... | C07K 14/705 514/44 A |
| 2013/0029972 A1 | 1/2013 | Hipskind | |

FOREIGN PATENT DOCUMENTS

| WO | WO 1998/28268 | 7/1998 |
|---|---|---|
| WO | WO 2010/075074 | 7/2010 |
| WO | WO 2011/060051 | 5/2011 |
| WO | WO 2012/097039 | 7/2012 |
| WO | 2013/016081 A1 | 1/2013 |
| WO | WO 2015/193352 | 12/2015 |
| WO | WO 2016/164580 | 10/2016 |
| WO | WO 2016/168014 | 10/2016 |
| WO | WO-2017/180385 | 10/2017 |
| WO | WO-2017/180389 | 10/2017 |
| WO | WO-2017/200969 | 11/2017 |
| WO | WO-2018/044662 | 3/2018 |
| WO | WO-2018/071307 | 4/2018 |
| WO | WO-2018/201056 | 11/2018 |

OTHER PUBLICATIONS

David C. Smith, A Phase I Dose Escalation and Expansion Study of the Anticancer Stem Cell Agent Demcizumab (Anti-DLL4) in Patients with Previously Treated Solid Tumors, Clin Cancer Res; 20(24) Dec. 15, 2014; Published OnlineFirst Oct. 16, 2014 (Year:2014).*
Juan Martin-Liberal, Leiomyosarcoma: Principles of management, Intractable & Rare Diseases Research. 2013; 2(4):127-129 (Year : 2013).*
Guijarro, Maria V. , Dual Pten/Tp53 Suppression Promotes Sarcoma Progression by Activating Notch Signaling (2013).
Guijarro, Maria V. Supplemental Figure S1, Guijarro, et al.
Guijarro, Maria V. Supplemental Figure S2 Guijarro, et al.
Guijarro, Maria V. Supplemental Figure S3 Guijarro, et al.
Guijarro, Maria V. Supplemental Figure S4 Guijarro, et al.
Guijarro, Maria V. Supplemental Table S1.
Guijarro, Maria V. Supplemental Table S2.
Guijarro, Maria V. Supplemental Table S3. Incidence of non-mesenchymal tumors.
Guijarro, Maria V. Supplemental Table S4.
Messersmith, Wells A. , A Phase 1 Dose-Finding Study in Patients with Advanced Solid Malignancies of the Oral y-Secretase Inhibitor PF-03084014, American Association for Cancer research, Sep. 17, 2014, pp. 60-68, Aurora, Colarado.
Messersmith, Wells A., Messersmith et al Supplemental Information Table.
Messersmith, Wells A., Supplemental Figure S1.
Dumont, Amaury G., Anti-Tumor effects of the Notch Pathway in gastrointestinal Stromal tumors, Texas Medical Center Library, Dec. 2012, Houston, Texas.
Gaducci, Angiolo, Pharmacological treatment for uterine leiomyosarcomas, Expert Opinion on Pharmacotherapy, Nov. 22, 2014, 335-346, 16:3.
Takebe, Naoko, Targeting Notch signaling pathway in cancer; Clinical development advances and challenges, Pharmacology & Therapeutics, 2014, 140-149, Elsevier Inc.
Bender, Mark H., Abstract 1131: Novel inhibitor of Notch signaling for the treatment of cancer, 2013, American Association for Cancer Research, Washington, DC.
Pant, Shubham, A first-in-human phase 1 study of oral Notch inhibitor LY900009 in patients with advanced cancer, Journal of Clincial Oncology, vol. 30, 2012.
U.S. Appl. No. 16/093,117, (Int'l) filed Apr. 5, 2017, Patel et al.
U.S. Appl. No. 16/093,123, (Int'l) filed Apr. 5, 2017, Beckman et al.
U.S. Appl. No. 16/301,360, (Int'l) filed May 16, 2017, Bender et al.

(Continued)

*Primary Examiner* — Sarah Pihonak
*Assistant Examiner* — Jason Deck
(74) *Attorney, Agent, or Firm* — Morrison & Foerster, LLP

(57) ABSTRACT

A method and medicament comprising 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide or a pharmaceutically acceptable salt or hydrate thereof for treating leiomyosarcoma is provided.

9 Claims, 1 Drawing Sheet

(56) References Cited

OTHER PUBLICATIONS

U.S. Appl. No. 16/328,267, (Int'l) filed Aug. 24, 2017, Benhadji et al.

Anonymous, "F525 Peripheral T-Cell Lymphoma Facts I p. 1 Revised," Leukemia & Lymphoma Society (2014) Retrieved on https://www.lls.org/sites/default/files/file_assets/peripheraltcell-lymphomafacts.pdf.

Anonymous, "Notch Inhibitor Shows Modest Efficacy," Cancer Discovery (2016) pp. 1-3. Retrieved on URL:http://cancerdiscovery.aacrjournals.org/content/early/2016/12/13/2159-8290.CD-NB2016-159.

Bell et al., "Expression and significance of Notch signaling pathway in salivary adenoid cystic carcinoma," Annals of Diagnostic Pathology, (2014) 18: 10-13.

Belyea et al, "Inhibition of the Notch-Hey1 Axis Blocks Embryonal Rhabdomyosarcoma Tumorigenesis," Clin Cancer Res, (2011) 17(23): 7324-7336.

Choi et al., "Correlation of computed tomography and positron emission tomography in patients with metastatic gastrointestinal stromal tumor treated at a single institution with imatinib mesylate: proposal of new computed tomography response criteria," J. Clin. Oncol., (2007) 25(13): 1753-1759.

Chou et al, "Quantitative analysis of dose-effect relationships: the combined effects of multiple drugs or enzyme inhibitors," Adv. Enzyme Regul., (1984) 22: 27-55.

Clinical Trial Identifier NCT/02079636. Updated Feb. 3, 2016. Retrieved from https://clinicaltrials.gov/archive/NCT02079636/2016_02_03.

Clinical Trial Identifier NCT02784795. "A Study of LY3039478 in Participants with Advanced or Metastatic Solid Tumors". Updated May 26, 2016. Retrieved from https://clinicaltrials.gov/archive/NCT02784795/2016_05_26.

Cullion et al., "Targeting the Notch1 and mTOR pathways in a mouse T-ALL model," Blood (2009) 113:6172-6181.

Database WPI, Week 201156, Thomas Scientific, London, GB; AN 2011-J01934, XP002771616, CN 102 085 372 (Inst Basic Medical Sci Chinese Acad Medi), Jun. 8, 2011 abstract.

Grabher et al., "Notch 1 activation in the molecular pathogenesis of T-cell acute lymphoblastic leukaemia," Nature Review Cancer, (2006) (6):347-359.

Gutierrez et al., "NOTCH and PI3K-AKT Pathways Intertwined," Cancer Cell (2007) 12:411-413.

Hill et al., "Gamma secretase inhibition increase recognition of multiple myeloma by BCMA-specific chimeric antigen receptor modified T cells," J Immunotherapy of Cancer (2017) 5(S2):5-6.

Holford et al., "Understanding the Dose-Effect Relationship," Clin. Pharmacokinet. (1981) 6: 429-453.

Joshi et al., "Notch signaling mediates G1/S cell-cycle progression in T cells via cyclin D3 and its dependent kinases," Blood, (2009) 113(8): 1689-1698.

Lipson et al., "Durable Cancer Regression Off-treatment and Effective Reinduction Therapy with an Anti-PD-1 Antibody," Clin Cancer Res (2013) 19(2):462-468.

Loewe et al., "Effect of combinations: Mathematical basis of problem," Arch. Exp. Pathol. Pharmacol., (1926) 114: 313-326.

Massard et al., "First-in-human study of LY3039478, a Notch signaling inhibitor in advanced or metastatic cancer," J Clin Oncol (2015) 33(15_suppl):2533.

Oken et al., "Toxicity and response criteria of the Eastern Cooperative Oncology Group," Am. J. Clin. Oncol., (1982) 5: 649-655.

Palomero et al., "Oncogenic NOTCH1 Control of MYC and PI3K: Challenges and Opportunities for Anti-NOTCH1 Therapy in T-Cell Acute Lymphoblastic Leukemias and Lymphomas," Clin. Cancer Res. (2008) 14(17):5314-5317.

Park et al., "Notch3 Gene Amplification in Ovarian Cancer," Cancer Research, (2006) 66: 6312-6318.

Ranganathan et al., "Notch signalling in solid tumours: a little bit of everything but not all the time," Nature Review Cancer, (2011) 11:338-351.

Rao et al., "Inhibition of NOTCH Signaling by Gamma Secretase Inhibitor Engages the RB Pathway and Elicits Cell Cycle Exit in T-Cell Acute Lymphoblastic Leukemia Cells," Cancer Res., (2009) 69(7): 3060-3068.

Robert-Moreno et al., "The notch pathway positively regulates programmed cell death during erythroid differentiation," Leukemia, (2007) 21: 1496-1503.

Roma et al., "Notch Pathway Inhibition Significantly Reduces Rhabdomyosarcoma Invasiveness and Mobility In Vitro," Clin Cancer Res, (2011) 17(3): 505-513.

Rosati et al, "Constitutively activated Notch signaling is involved in survival and apoptosis resistance of B-CLL cells," Blood, (2009) 113: 856-865.

Sekiya et al., "Intrahepatic cholangiocarcinoma can arise from Notch-mediated conversion of hepatocytes," J Clin Invest, (2012) 122(11): 3914-3918.

Shepard et al., "PI3K/mTOR inhibition upregulates NOTCH-MYC signalling leading to an impaired cytotoxic response," Leukemia (2013) 27:650-660.

Sliwa et al. "Hyperexpression of NOTCH-1 is found in immature acute myeloid leukemia." Int J Clin Exp Pathol, (2014) 7(3)): 882-889.

Takebe et al., "Targeting Notch signaling pathway in cancer: Clinical development advances and challenges," Pharmacol Ther (2014) 141(2):140-149.

Tejada et al., "The challenge of targeting Notch in hematologic malignancies," Frontiers in Pediatrics (2014) 2:1-8.

Villanueva et al., "Notch Signaling is Activated in Human Hepatocellular Carcinoma and Induces Tumor Formation in Mice," Gastroenterology, (2012) 143: 1660-1669.

Wang et al., "Hedgehog and Notch Signaling Regulate Self-Renewal of Undifferentiated Pleomorphic Sarcomas," Cancer Res, (2012) 72: 1013-1022.

Wen et al., "Updated Response Assessment Criteria for High-Grade Gliomas: Response Assessment in Neuro-Oncology Working Group," J. Clin. Oncol., (2010) 28(11): 1963-1972.

Weng et al., "Activating mutations of NOTCH1 in human T cell acute lymphoblastic leukemia," Science, (2004) 306(5694):269-271.

Westhoff et al., "Alterations of the Notch pathway in lung cancer," PNAS, (2009) 106: 22293-22298.

Worcester, "GSI inhibition may boost BCMA CAR T-cell therapy efficacy in myeloma," Hematology News. Published on Nov. 27, 2017. Retrieved on https://www.mdedge.com/hematology-oncology/article/152733/multiple-myeloma/gsi-inhibition-may-boost-bcma-car-t-cell-therapy.

Wu et al., "Clinicopathological significance of aberrant Notch receptors in intrahepatic cholangiocarcinoma," Int J Exp Pathol, (2014) 7(6): 3272-3279.

Yoon et al., "Clinicopathological significance of altered Notch signaling in extrahepatic cholangiocarcinoma and gallbladder carcinoma," World J Gastroenterol, (2011) 17(35): 4023-4030.

Yuen et al., "Abstract CT048: Population pharmacokinetics and pharmacodynamics for an oral Notch inhibitor, LY3039478, in the first-in-man study," Cancer Research (2016) 76(14):CT048.

* cited by examiner

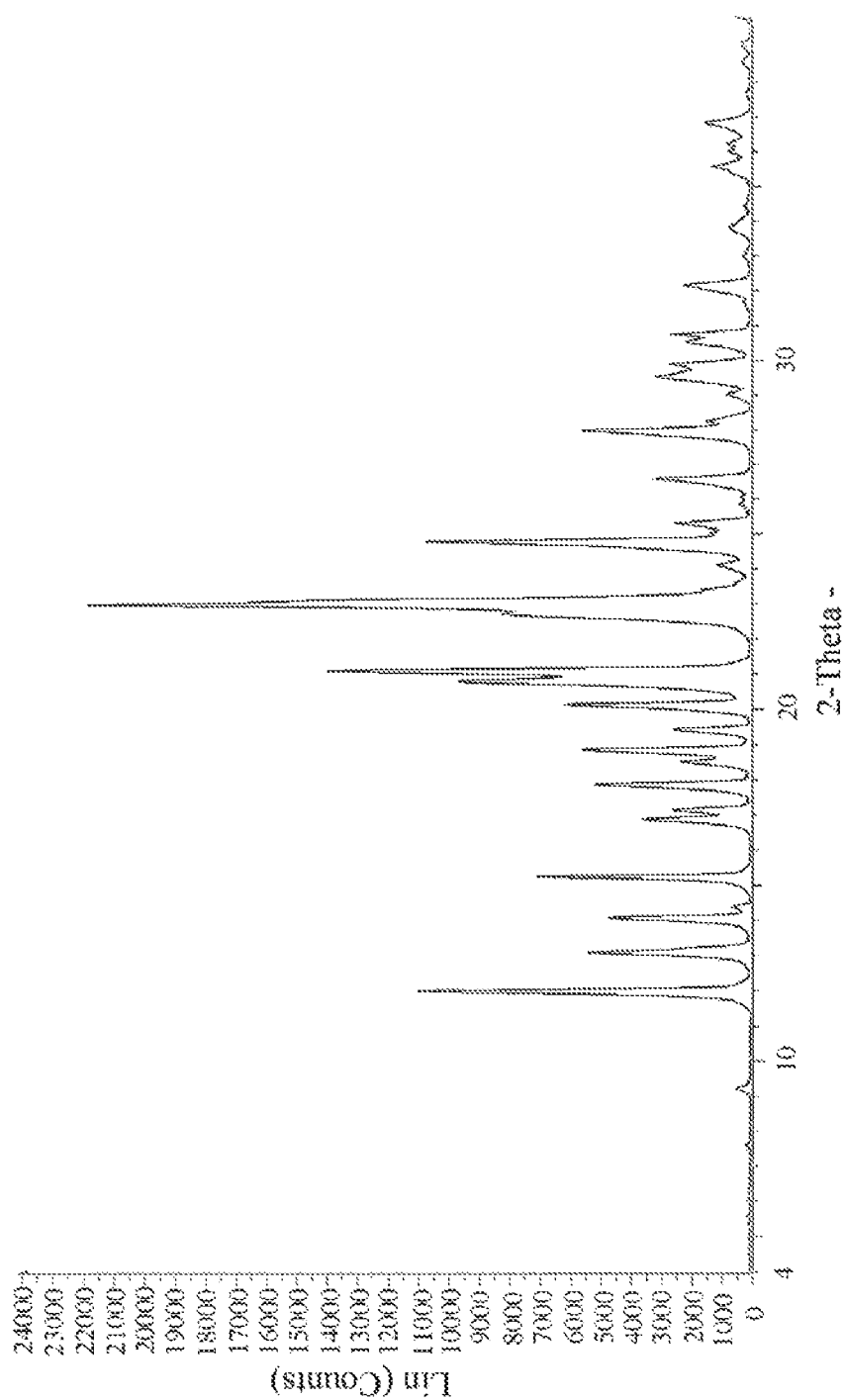

TARGETED TREATMENT OF LEIOMYOSARCOMA

Leiomyosarcoma (LMS) is an aggressive soft tissue sarcoma derived from smooth muscle cells typically of uterine, gastrointestinal or soft tissue origin. LMS tumors are frequently difficult to treat. The prognosis is poor, with survival rates among the lowest of all soft tissue sarcomas.

Treatment regimens generally comprise surgical excision or resection with wide margins. Radiation therapy and chemotherapy (or target treatments), such as doxorubicin, ifosfamide, gemcitabine and docetaxel, dacarbazine, ecteinascidin and pazopanib may be used pre-operatively in an effort to achieve a wide surgical margin or post-operatively to slow progression of systemic disease.

Notch signaling is an evolutionary conserved pathway that plays an integral role in development and tissue homeostasis in mammals. The Notch receptors and ligands contain single-pass transmembrane domains, are expressed on the cell surface and, for that reason, Notch signaling is particularly important in mediating communication between adjacent cells expressing the receptors and ligands. There are four known Notch receptors found in rodents and humans, termed Notch 1 to Notch 4. The Notch receptors are heterodimeric proteins composed of extracellular and intracellular domains that are initially synthesized as a single polypeptide. Receptor-ligand interaction triggers a series of proteolytic cleavages of the Notch receptor polypeptide in which γ-secretase activity is involved. γ-Secretase activity cleaves Notch intracellular domain from the cell surface which translocates to the nucleus to form a transcription factor complex. Notch intracellular domain (NICD) is the active form of the protein. Various Notch signaling functions include proliferation, differentiation, apoptosis, angiogenesis, migration and self-renewal. These diverse roles of Notch signaling during the development and maintenance of normal tissues are aberrantly activated in different forms of cancer. The oncogenic functions of Notch signaling include the inhibition of apoptosis and the promotion of cell proliferation.

Recently, a specific Notch pathway signaling inhibitory compound having activity against various tumor types has been disclosed in WO 2013/016081.

There is a need for therapeutic agents that exhibit activity (efficacy) in the treatment of LMS. There is also a need for an alternative therapeutic agent to those currently used to treat LMS. The Notch inhibitor 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, is an alternative therapeutic agent and evidences surprising and unexpected clinical therapeutic activity against LMS.

FIG. 1 is a representative X-ray powder diffraction pattern for the compound of Example 2.

One aspect of the invention provides a method of treating a patient suffering from LMS comprising administering to an LMS patient in need of treatment an effective amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof.

Another aspect of the invention provides a method of treating a patient suffering from LMS comprising administering to an LMS patient in need of treatment 2.5 to 100 mg/dose of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide or a pharmaceutically acceptable salt or hydrate thereof.

A further aspect of the invention provides a method of treating a patient suffering from LMS comprising administering to an LMS patient in need of treatment 10 to 75 mg/dose of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide or a pharmaceutically acceptable salt or hydrate thereof.

Another aspect of the invention provides a method of treating a patient suffering from LMS comprising administering to an LMS patient in need of treatment 25 to 75 mg/dose of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide or a pharmaceutically acceptable salt or hydrate thereof.

A further aspect of the invention provides a method of treating a patient suffering from LMS comprising administering to an LMS patient in need of treatment an effective amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide or a pharmaceutically acceptable salt or hydrate thereof T.I.W.

Another aspect of the invention provides a compound or a pharmaceutically acceptable salt thereof for use in the treatment of leiomyosarcoma, wherein the compound is 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide.

A further aspect of the invention provides a compound or a pharmaceutically acceptable salt thereof for use in the treatment of leiomyosarcoma, wherein the compound is 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide wherein the dose administered is 2.5 to 100 mg.

Another aspect of the invention provides a compound or a pharmaceutically acceptable salt thereof for use in the treatment of leiomyosarcoma, wherein the compound is 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide wherein the dose administered is 10 to 75 mg.

A further aspect of the invention provides a compound or a pharmaceutically acceptable salt thereof for use in the treatment of leiomyosarcoma, wherein the compound is 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide wherein the dose administered is 25 to 75 mg.

Another aspect of the invention provides a compound or a pharmaceutically acceptable salt thereof for use in the treatment of leiomyosarcoma, wherein the compound is 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide wherein the dose administration is T.I.W.

A further aspect of the invention provides the use of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, for preparation of a medicament for treatment of LMS.

Another aspect of the present invention provides 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof together with a pharmaceutically acceptable carrier and optionally other therapeutic ingredients for treatment of LMS.

The compound 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide is taught to be a Notch inhibitor in WO 2013/016081. The name identifies a compound having the following structure:

Compound 1

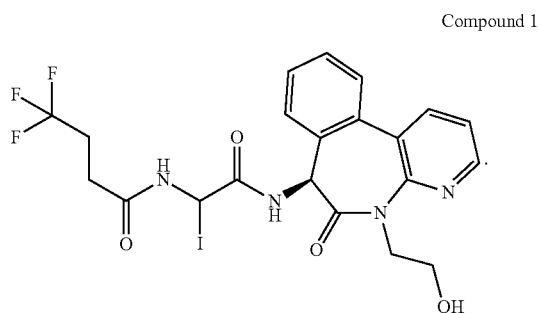 [SMILES: O=C(CCC(F)(F)F)NC(I)C(=O)N[C@@H]1C(=O)N(CCO)c2ncccc2-c2ccccc21]

"Therapeutically effective amount" or "effective amount" means the dosage of Compound 1, or pharmaceutically acceptable salt or hydrate thereof, or pharmaceutical composition containing the compound, or pharmaceutically acceptable salt or hydrate thereof, necessary to inhibit Notch signaling in an LMS patient, and either destroy the target cancer cells or slow or arrest the progression of the cancer in a patient. Anticipated dosages of Compound 1 or a pharmaceutically acceptable salt or hydrate thereof in an adult are in the range of 2.5 to 100 mg/dose. Preferred dosages are anticipated to be in the range of 10 to 75 mg/dose. Most preferred dosages are anticipated to be in the range of 25 to 75 mg/dose. In a pediatric patient, dosages may be lower and are anticipated to be based on surface area. The exact dosage required to treat a patient and the length of treatment time will be determined by a physician in view of the age, stage and severity of the disease as well as the specific needs and response of the individual patient. Although administration on a per day basis in the above ranges is contemplated, the administration regimen may be adjusted to provide a more optimal therapeutic benefit to a patient and to manage and ameliorate observed side effects, for example mucoid enteropathy (hypersecretion and accumulation of mucus in the gastrointestinal tract) or symptoms related to tumor necrosis. In addition to daily administration, administration every other day (Q2D); every other day over a five day period followed by two days without administration (T.I.W.); or every third day (Q3D) may be appropriate. An administration regimen of T.I.W. is preferred during a 28-day cycle, along with administration (pre-, concomitant, or post-administration of Compound 1) on an as needed basis of a steroid, preferably a corticosteroid, and most preferably dexamethasone to manage or ameliorate mucoid enteropathy. Each or both of the dosage and administration schedule, or cycle, may be modified at the discretion of a physician due to tumor necrosis or other factors.

The terms "treatment," "treat," and "treating," are meant to include the full spectrum of intervention for the cancer from which the patient is suffering, such as administration of the active compound to alleviate to slow or reverse one or more of the symptoms and to delay progression of the cancer even if the cancer is not actually eliminated. The patient to be treated is a mammal, in particular a human.

The compound of the present invention is preferably formulated as a pharmaceutical composition using a pharmaceutically acceptable carrier and administered by a variety of routes. Preferably, such compositions are for oral administration. Such pharmaceutical compositions and processes for preparing them are well known in the art. See, e.g., REMINGTON: THE SCIENCE AND PRACTICE OF PHARMACY (A. Gennaro, et al., eds., 19$^{th}$ ed., Mack Publishing Co., 1995). In a particular embodiment, the pharmaceutical composition comprises 4,4,4-trifluoro-N-[(1S)-2-[[(7S)-5-(2-hydroxyethyl)-6-oxo-7H-pyrido[2,3-d][3]benzoazepin-7-yl]amino]-1-methyl-2-oxo-ethyl]butanamide, or a pharmaceutically acceptable salt or hydrate thereof, and a pharmaceutically acceptable carrier. The present invention also provides pharmaceutical compositions comprising 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof with a pharmaceutically acceptable carrier and one or more other therapeutic agents.

The compound of the present invention is capable of reaction with a number of inorganic and organic acids to form pharmaceutically acceptable acid addition salts. Such pharmaceutically acceptable salts and common methodology for preparing them are well known in the art. See. e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977.

As used herein, the term "patient" means mammal; "mammal" means the Mammalia class of higher vertebrates; and the term "mammal" includes, but is not limited to, a human.

Compound 1, or a pharmaceutically acceptable salt or hydrate thereof, may be prepared by a variety of procedures known in the art, as well as those described below. The specific synthetic steps may be combined in different ways to prepare Compound 1, or a pharmaceutically acceptable salt or hydrate thereof.

Compound 1 is named: 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide; and may also be named: N-[(1S)-2-[[(7S)-6,7-dihydro-5-(2-hydroxyethyl)-6-oxo-5H-pyrido[3,2-a][3]benzazepin-7-yl]amino]-1-methyl-2-oxoethyl]-4,4,4-trifluorobutanamide; and other names may be used to unambiguously identify Compound 1.

It will be understood Compound 1 is depicted as a single stereoisomer. There are two chiral centers giving rise to four stereoisomers. As used herein, references to Compound 1 are meant to also include racemic mixtures including Compound 1. Herein, the Cahn-Ingold-Prelog designations of (R)- and (S)- are used to refer to specific isomers. Specific stereoisomers can be prepared by stereospecific synthesis using enantiomerically pure or enriched starting materials. The specific stereoisomers of either starting materials, intermediates, or racemic mixtures including Compound 1 can be resolved by techniques well known in the art, such as those found in *Stereochemistry of Organic Compounds*, E. I. Eliel and S. H. Wilen (Wiley 1994) and *Enantiomers, Racemates, and Resolutions*, J., Jacques, A. Collet, and S. H. Wilen (Wiley 1991), including chromatography on chiral stationary phases, enzymatic resolutions, or fractional crystallization or chromatography of diastereomers formed for that purpose, such as diastereomeric salts. While all mixtures containing the compound of the present invention are contemplated within the present invention, the preferred embodiment is Compound 1.

It has also been found that Compound 1 exists as atropisomers, or specific conformers. In aqueous solutions, 8-9% of atropisomer 2 (minor atropisomer) is detected by $^1$H NMR and LC-MS in equilibrium with atropisomer 1 (major atropisomer) at ambient temperature after 24 hours. In organic solvents, at ambient temperature after 24 hours, approximately 1-2% of atropisomer 2 is detected by $^1$H NMR and LC-MS in equilibrium with atropisomer 1. Although detectable by $^1$H NMR and LC-MS analysis, atropisomer 2 is not isolable.

The compounds employed as initial starting materials in the synthesis of the compound of the present invention are well known and, to the extent not commercially available, are readily synthesized using specific references provided, by standard procedures commonly employed by those of ordinary skill in the art or are found in general reference texts.

Examples of known procedures and methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5$^{th}$ Edition, Michael B. Smith and Jerry March, Wiley Interscience, 2001; Advanced Organic Chemistry, 4$^{th}$ Edition, Part B, Reactions and Synthesis, Francis A. Carey and Richard J. Sundberg, Kluwer Academic/Plenum Publishers, 2000, etc., and references cited therein.

The intermediates and Compound 1 are named using a SymaxDraw version 3.2 Drawing Program, from the structures, as the IUPAC name consistently applied.

PREPARATION 1

Benzyl (2S)-2-(4,4,4-trifluorobutanoylamino)propanoate

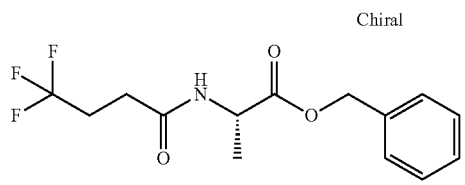 [SMILES: C[C@H](NC(=O)CCC(F)(F)F)C(=O)OCc1ccccc1]

Add successively L-alanine benzyl ester hydrochloride (7.00 g, 32.5 mmol), diisopropylethylamine (28.30 mL, 162.3 mmol), 1-hydroxybenzotriazole hydrate (7.46 g, 48.7 mmol) and 1-(3-dimethylaminopropyl)-3-ethylcarbodiimide hydrochloride (9.33 g 48.7 mmol) to a solution of 4,4,4-trifluorobutyric acid (7.131 g, 48.7 mmol) in dichloromethane (162 mL) at ambient temperature under nitrogen and stir for 20 hours. Add a 20% aqueous solution of citric acid (150 mL, 162 mmol), stir mixture for 5 minutes and separate layers. Extract from aqueous with dichloromethane (100 mL). Wash combined organics with saturated aqueous solution of sodium bicarbonate (150 mL), dry over magnesium sulfate and concentrate. Purify the residue by flash chromatography, eluting with hexane:ethyl acetate (4:1 to 2:1) to give the title compound as a white solid (9.22 g, 30.4 mmol, 94%). MS (m/z): 304 (M+1); $[\alpha]_{Na}^{25}=-44.6°$ (c=5.0, methanol).

PREPARATION 2

(2S)-2-(4,4,4-Trifluorobutanoylamino)propanoic Acid

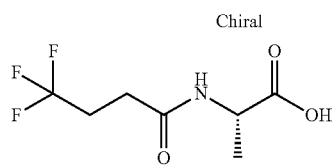

Add palladium/carbon (5%, 1.76 g, 0.8 mmol) in one portion to a solution of benzyl (2S)-2-(4,4,4-trifluorobutanoylamino)propanoate (8.80 g, 29 mmol) in methanol (88 mL) at ambient temperature. Degas the mixture (vacuum/nitrogen), fill with hydrogen (one atmosphere) and stir under hydrogen (29 mmol) for 5 hours. Filter through Celite®, rinse filter cake with methanol and concentrate the filtrate to obtain the title compound as a white solid (6.11 g, 28.7 mmol, 99%). MS (m/z): 214 (M+1); $[\alpha]_{Na}^{25}=-24.7°$ (c=5.0, methanol).

PREPARATION 3

Methyl 2-(2-bromophenyl)acetate

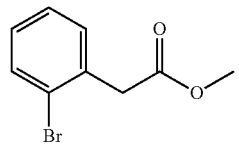

Add dimethylformamide (2.1 mL, 27.3 mmol) followed by thionyl chloride (52.3 mL, 717.8 mmol) over 7 minutes to a solution of 2-bromophenylacetic acid (150.0 g, 683.6 mmol) in dichloromethane (1.50 L) cooled with an ambient temperature water bath. Stir mixture for 5 hours, add methanol (41.5 mL, 1.0 mol) over 5 minutes. Bubble nitrogen through solution overnight. Concentrate to obtain the title compound as a colorless oil in quantitative yield (166.0 g, 724.7 mmol). 1H NMR (300 MHz, CDCl$_3$): 7.57 (d, J=7.9 Hz, 1H), 7.30-7.26 (m, 2H), 7.19-7.12 (m, 1H), 3.80 (s, 2H), 3.72 (s, 3H).

PREPARATION 4

Methyl 2-[2-(4,4,5,5-tetramethyl-1,3,2-dioxaborolan-2-yl)phenyl]acetate

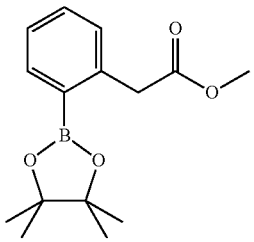

Degas a suspension of methyl 2-(2-bromophenyl)acetate (156.6 g, 684 mmol), bis(pinacolato)diboron (194.9 g, 752 mmol), and potassium acetate (135.6 g, 1.4 mol) in N-methylpyrrolidone (940 mL) with three vacuum/nitrogen cycles. Add (1,1'-bis(diphenylphosphino)ferrocene)palladium(II) chloride (11.4 g, 13.7 mmol) and heat at 80° C. After 15 hours add (1,1'-bis(diphenylphosphino)ferrocene)palladium (II) chloride (11.4 g, 13.7 mmol) and stir at 90° C. for 24 hours. Cool to ambient temperature and pour over a mixture of ice and water (3 L), and methyl tertiary butyl ether (1 L) was added. Stir mixture, filter through a pad of Celite® and separate layers. Extract from aqueous with methyl tertiary butyl ether (2×500 mL). Wash combined organics with water (2×500 mL), brine (500 mL), dry over sodium sulfate and concentrate. Purify the residue by flash chromatography, eluting with hexane:ethyl acetate (9:1) to give the title compound as a white solid (160.6 g, 581.6 mmol, 85%). MS (m/z): 277 (M+1).

PREPARATION 5

5,7-Dihydropyrido[2,3-d][3]benzazepin-6-one

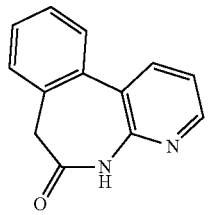 [SMILES: O=C1Cc2ccccc2-c2cccnc2N1]

Add potassium carbonate (235.7 g, 1.71 mol) to a solution of 2-amino-3-bromopyridine (88.5 g, 511.7 mmol) in 1,4-dioxane (550 mL) and water (550 mL). Degas the mixture with three cycles of vacuum/nitrogen, add palladium (II) acetate (6.4 g, 28.4 mmol) and tri-t-butylphosphonium tetrafluoroborate (16.5 g, 56.9 mmol) and stir under nitrogen at 88° C. Add a solution of methyl 2-[2-(4,4,5,5-tetramethyl-1,3,2-dioxaborolan-2-yl)phenyl]acetate (157.0 g, 568.5 mmol) in 1,4-dioxane (550 mL) dropwise over three minutes and stir the mixture at 88° C. for 20 minutes. Cool mixture to 50° C., add water (100 mL), and separate layers. Extract from aqueous with ethyl acetate (2×100 mL), dry combined organics over sodium sulfate and concentrate. Dissolve the concentrated material in N-methylpyrrolidone (314 mL), cool in ice bath and add sulfuric acid (314 mL, 5.9 mol) dropwise to maintain a temperature of approximately 45° C. Stir mixture at 140° C. for 90 minutes. Cool to ambient temperature, add ice (4 kg) and basify with portion wise addition of 50% aqueous NaOH solution until solution is pH 7-8. Cool suspension to 10-15° C., filter out solids and wash with water (2 L), hexanes (1 L) and methyl tertiary butyl ether (1 L). Dry under vacuum at 40° C. Treat material with refluxing mixture of 10% methanol/dichloromethane solution and filter hot (×4). Concentrate combined filtrates to afford the title compound as a light brown solid (85 g, 404.3 mmol, 71%). MS (m/z): 211 (M+1).

PREPARATION 6

5-[2-(tert-Butyl(dimethyl)silyl)oxyethyl]-7H-pyrido[2,3-d][3]benzazepin-6-one

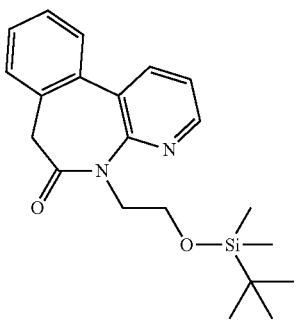 [SMILES: CC(C)(C)[Si](C)(C)OCCN1C(=O)Cc2ccccc2-c2cccnc21]

Add cesium carbonate (186.6 g, 572.7 mmol), (2-bromoethoxy)-tert-butyldimethylsilane (88.0 mL, 409.1 mmol), and sodium iodide (6.1 g, 40.9 mmol) to a suspension of 5,7-dihydropyrido[2,3-d][3]benzazepin-6-one (86.0 g, 409.1 mmol) in dimethylformamide (860 mL) and stir at 70° C. for 20 hours. Cool mixture to ambient temperature, pour over ice and water (100 mL), add ethyl acetate (200 mL). Filter mixture through Celite®, then wash with ethyl acetate (100 mL). Separate layers of filtrate, extract from aqueous with ethyl acetate (2×50 mL). Wash combined organics with water (2×100 mL), brine (100 mL), dry over sodium sulfate and concentrate. Dissolve material in tetrahydrofuran (1.28 L), add Silia® bond palladium scavenger (16.7 g) and stir at ambient temperature for 20 hours. Filter through a pad of silica, wash with tetrahydrofuran (200 mL) and concentrate to obtain the title compound (155 g, 420.6 mmol) as a light brown oil that crystallizes in quantitative yield. MS (m/z): 369 (M+1).

Method 2:

Heat a mixture 5,7-dihydropyrido[2,3-d][3]benzazepin-6-one (22.5 g, 106.9 mmol) and dimethylformamide (500 mL) to 100° C. for 5 minutes. Cool to 40° C., add cesium carbonate (104.3 g, 320.1 mmol) and (2-bromoethoxy)-tert-butyldimethylsilane (29.9 mL, 138.9 mmol) and stir at ambient temperature overnight. Heat to 60° C. for approximately 2 hours, and then cool to ambient temperature. Partition the residue between ethyl acetate (1 L) and water (3 L), back extract from aqueous layer with ethyl acetate (2×500 mL), wash combined organics with brine (2×500 mL). Dry combined organics over sodium sulfate and concentrate. Purify the residue by flash chromatography, eluting with ethyl acetate:hexane (0:100 to 100:0) to give the title compound as an oil (39.4 g, 106.9 mmol, 89%). MS (m/z): 369 (M+1).

PREPARATION 7

5-[2-(tert-Butyl(dimethyl)silyl)oxyethyl]-7-hydroxy-imino-pyrido[2,3-d][3]benzazepin-6-one

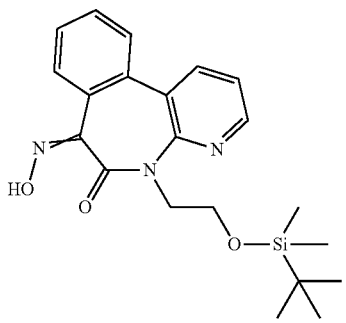 [SMILES: CC(C)(C)[Si](C)(C)OCCn1c(=O)c(=NO)c2ccccc2c2cccnc21]

Add potassium 2-methylpropan-2-olate (66.1 g, 588.8 mmol) to a solution of 5-[2-(tert-butyl(dimethyl)silyl)oxyethyl]-7H-pyrido[2,3-d][3]benzazepin-6-one (155.0 g, 420.6 mmol) in tetrahydrofuran (1.6 L) at −5° C. and stir for 10 minutes. Add isoamyl nitrite (61.9 mL, 462.6 mmol) dropwise at −5° C. and stir mixture for 10 minutes. Pour over ice/water (2 L) and extract with ethyl acetate (3×200 mL). Wash combined organics with brine (200 mL), dry over sodium sulfate. Add toluene (1 L) and concentrate (×3) to obtain the title compound as a thick brown oil (160.0 g, 402.5 mmol, 96%). MS (m/z): 398 (M+1).

PREPARATION 8

(7S)-7-Amino-5-(2-hydroxyethyl)-7H-pyrido[2,3-d][3]benzazepin-6-one

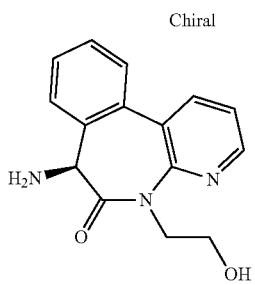 [SMILES: N[C@@H]1C(=O)N(CCO)c2ncccc2-c2ccccc21]

Chiral

Add trifluoroacetic acid (124.0 mL, 1.64 mol) in several portions to a solution of 5-[2-(tert-butyl(dimethyl)silyl)oxyethyl]-7-hydroxyimino-pyrido[2,3-d][3]benzazepin-6-one (155.0 g, 389.9 mmol) in a mixture of dichloromethane (620 mL) and methanol (310 mL) in an ambient temperature water bath. Add zinc (76.5 g, 1.2 mol) in several portions so that internal temperature was maintained at 33-38° C. Stir for 15 hours at ambient temperature. Filter mixture through Celite®, wash with 10% methanol/dichloromethane (100 mL) and concentrate the filtrate. Add dichloromethane (0.5 L) and ice (500 g), stir and basify with a 50% aqueous solution of NaOH. Filter out solids, separate filtrate layers. Extract from aqueous with dichloromethane (2×100 mL), and concentrate combined organics. Slurry solids in hexane, and then filter and dry under high vacuum to obtain the racemate of the title compound as a light yellow solid (74.0 g, 274.8 mmol, 71%). Purify the material on a Chiralpak® AD column eluting with ethanol (0.2% dimethethylamine):acetonitrile (0:100 to 100:0) to obtain the title compound (35.0 g, 130 mmol, 33.3%) as a white solid. MS (m/z): 270 (M+1); $[\alpha]_{Na}^{25}$=+187.83° (c=6.9, methanol).

PREPARATION 9

7-Azido-5-[2-(tert-butyl(dimethyl)silyl)oxyethyl]-7H-pyrido[2,3-d][3]benzazepin-6-one

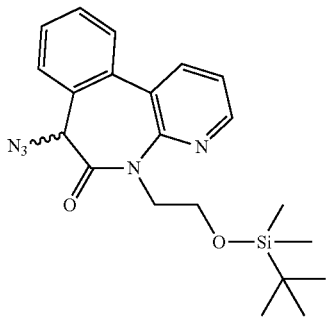 [SMILES: CC(C)(C)[Si](C)(C)OCCN1C(=O)C(N=[N+]=[N-])c2ccccc2-c2cccnc21]

Wash potassium hydride (approximately 2 scoops, 35 weight % in mineral oil) with hexanes and decant to remove oil, add tetrahydrofuran (60 mL) and cool to −78° C. Dry a solution of 2,4,6-tris(1-methylethyl)-benzenesulfonyl azide (37.6 g, 121.6 mmol) in tetrahydrofuran (60 mL) over sodium sulfate for 45 minutes. Decant azide solution into the potassium hydride suspension over 15 minutes. Remove cold bath and allow it to warm to ambient temperature for 45 minutes; set aside dry solution. Cool a solution of diisopropylamine (17.0 mL, 121.0 mmol) and tetrahydrofuran (50 mL) to −78° C., add n-butyl lithium (52.1 mL, 130.3 mmol) dropwise over 5 minutes. Remove cold bath and allow it to warm for 15 minutes then cool back to −78° C. Cannulate into a −78° C. solution of 5-[2-(tert-butyl(dimethyl)silyl)oxyethyl]-7H-pyrido[2,3-d][3]benzazepin-6-one (34.3 g, 93.1 mmol) in tetrahydrofuran (400 mL) over 5-10 minutes. Stir for one hour at −78° C. then remove cold bath and allow it to warm for 15 minutes (to approximately −45° C.). Cool to −78° C. and add the dried 2,4,6-tris(1-methylethyl)-benzenesulfonyl azide solution via cannula over 5-10 minutes. Remove bath and allow to warm to −5 to 0° C. over 1 hour. Cool in ice/water bath and add acetic acid (26.7 mL, 465.3 mmol) dropwise over 13 minutes. Allow to warm to ambient temperature over 65 minutes and quench with saturated sodium bicarbonate solution (1 L). Dilute reaction with ethyl acetate (600 mL) and water (2 L), separate layers, back extract from aqueous with ethyl acetate (2×400 mL). Wash combined organics with saturated aqueous sodium bicarbonate solution (500 mL) and brine (500 mL), dry over sodium sulfate and concentrate. Purify the residue by flash chromatography, eluting with ethyl acetate:hexane (0:100 to 100:0) to give the title compound as an oil (39.8 g, 92.3 mmol, 99%). MS (m/z): 410 (M+1).

PREPARATION 10

7-Amino-5-[2-(tert-butyl(dimethyl)silyl)oxyethyl]-7H-pyrido[2,3-d][3]benzazepin-6-one

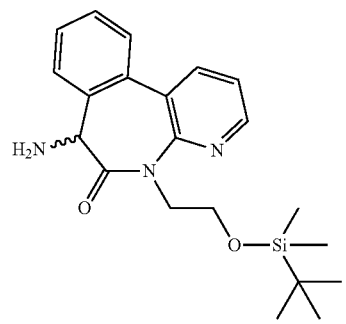

Add palladium/carbon (2.2 g, 1.0 mmol, 5% on carbon) to a nitrogen purged solution of 7-azido-5-[2-(tert-butyl(dimethyl)silyl)oxyethyl]-7H-pyrido[2,3-d][3]benzazepin-6-one (39.8 g, 92.3 mmol) in ethanol (923 mL). Evacuate/fill with hydrogen three times and stir under hydrogen (one atmosphere) at ambient temperature overnight. Filter over Celite®, rinse with ethanol and ethyl acetate and concentrate to obtain the title compound as a transparent oil (36.6 g, 89.9 mmol, 97%). MS (m/z): 384 (M+1).

PREPARATION 11 tert-Butyl N-[(1S)-2-[[5-[2-(tert-butyl(dimethyl)silyl)oxyethyl]-6-oxo-7H-pyrido[2,3-d][3]benzazepin-7-yl]amino]-1-methyl-2-oxo-ethyl]carbamate

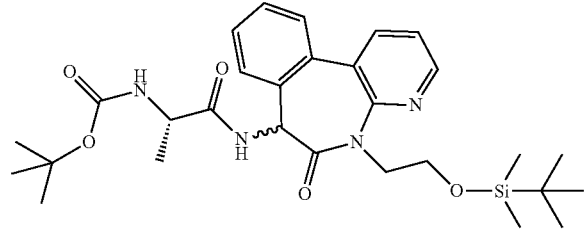 [SMILES: C[C@H](NC(=O)OC(C)(C)C)C(=O)NC1C(=O)N(CCO[Si](C)(C)C(C)(C)C)c2ncccc2-c2ccccc21]

Cool a mixture of 7-amino-5-[2-(tert-butyl(dimethyl)silyl)oxyethyl]-7H-pyrido[2,3-d][3]benzazepin-6-one (36.3 g, 89.9 mmol), dichloromethane (360 mL), triethylamine (16.3 mL, 116.9 mmol), 3-hydroxytriazolo[4,5-b]pyridine (15.9 g, 116.9 mmol), and (2S)-2-(tert-butoxycarbonylamino)propanoic acid (22.5 g, 116.9 mmol) to 0° C. Add 1-(3-dimethylaminopropyl)-3-ethylcarbodiimide hydrochloride (22.4 g, 116.9 mmol) and after 5 minutes allow to warm to ambient temperature overnight. Wash with water (500 mL×2), saturated aqueous sodium bicarbonate solution (2×300 mL), brine (300 mL), and then dry over sodium sulfate and concentrate. Purify the residue by flash chromatography, eluting with isopropyl alcohol:hexane (5:95 to 10:90) to give the title compound as a white foam (43.14 g, 77.77 mmol, 86.50%). MS (m/z): 555 (M+1).

PREPARATION 12

(2S)-2-Amino-N-[5-(2-hydroxyethyl)-6-oxo-7H-pyrido[2,3-d][3]benzazepin-7-yl]propanamide

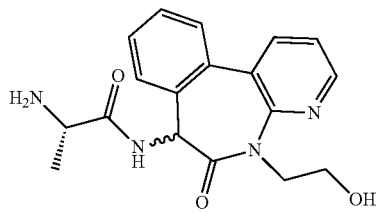 [SMILES: C[C@H](N)C(=O)NC1C(=O)N(CCO)c2ncccc2-c2ccccc21]

Add trifluoroacetic acid (30 mL, 396.76 mmol) over 5 minutes to a 0° C. solution of tert-butyl N-[(1S)-2-[[5-[2-(tert-butyl(dimethyl)silyl)oxyethyl]-6-oxo-7H-pyrido[2,3-d][3]benzazepin-7-yl]amino]-1-methyl-2-oxo-ethyl]carbamate (5.56 g, 10.0 mmol) and dichloromethane (30 mL) and allow to warm and stir at ambient temperature for 5 hours. Purify the residue by flash chromatography via SCX® columns (Isolute SCX-2×6) eluting with methanol followed by ethyl acetate:methanol (2N ammonia) (1:1) to obtain the title compound as a white solid (3.48 g, 10.2 mmol) in quantitative yield. MS (m/z): 341 (M+1).

EXAMPLE 1

4,4,4-Trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide

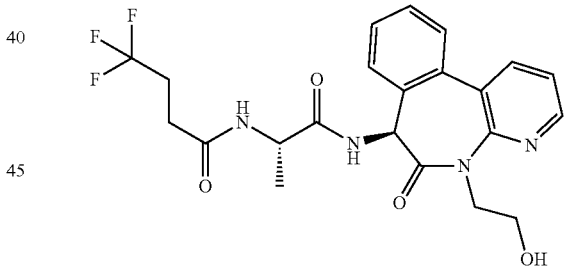

Add (2S)-2-(4,4,4-trifluorobutanoylamino)propanoic acid (28.9 g, 135.7 mmol; prepared substantially as described above in Preparation 2), 1-(3-dimethylaminopropyl)-3-ethylcarbodiimide hydrochloride (29.7 g, 155.1 mmol) sequentially to a suspension of (7S)-7-amino-5-(2-hydroxyethyl)-7H-pyrido[2,3-d][3]benzazepin-6-one (34.8 g, 129.2 mmol) in dichloromethane (696 mL) at 0° C., stir for 5 minutes. Add 1-hydroxybenzotriazole monohydrate (24.7 g, 155.1 mmol), allow it to stir for one hour, and then warm to ambient temperature. Add (2S)-2-(4,4,4-trifluorobutanoylamino)propanoic acid (0.6 g, 2.6 mmol) and stir for 15 minutes at ambient temperature. Add water (600 ml), filter out white solid, and separate layers of filtrate. Wash organic layer with water (3×200 mL), dry over sodium sulfate and concentrate to afford a light brown foam. Slurry material in 50% methyl tertiary butyl ether hexanes (500 mL), filter out solids, dry under high vacuum to obtain 65 g solids.

Add water (195 mL) and potassium bicarbonate (14.0 g, 140.0 mmol) to a 10° C. solution of the previously obtained solids (65.0 g, 140.0 mmol) in methanol (195 mL) and stir at ambient temperature for 29 hours. Concentrate and extract with dichloromethane (3×50 mL). Wash combined organics with water (3×20 mL), dry over sodium sulfate and concentrate. Purify the residue by flash chromatography eluting with methanol:dichloromethane (98:2, 7N in ammonia). Triturate material from 50% methyl tertiary butyl ether/hexane, then triturate from methyl tertiary butyl ether (500 ml). Wash solids with methyl tertiary butyl ether (200 mL) and hexane (200 mL) and dry solids under high vacuum to obtain the title compound as an off-white solid (42.0 g, 90.4 mmol, 65%). MS (m/z): 270 (M+1); $[\alpha]_{Na}^{25}=-153.40°$ (c=5.0, methanol).

Method 2:

Add 1-(3-dimethylaminopropyl)-3-ethylcarbodiimide hydrochloride (2.50 g, 13.0 mmol) to a 0° C. mixture of (2S)-2-amino-N-[5-(2-hydroxyethyl)-6-oxo-7H-pyrido[2,3-d][3]benzazepin-7-yl]propanamide (3.4 g, 10.0 mmol), dichloromethane (40 mL), 3-hydroxytriazolo[4,5-b]pyridine (1.8 g, 13.0 mmol), 4,4,4-trifluorobutanoic acid (1.9 g, 13.0 mmol), and triethylamine (1.8 mL, 13.0 mmol). Allow to stir and warm to ambient temperature overnight. Add water (40 mL) and partition between dichloromethane (100 mL) and water (50 mL). Separate layers, back extract from aqueous with dichloromethane, wash combined organic layers with saturated aqueous sodium bicarbonate solution (2×100 mL). Back extract from bicarbonate layers with dichloromethane (25 mL), dry combined organic layers over sodium sulfate and concentrate. Purify the residue by flash chromatography, eluting with methanol (2N ammonia):dichloromethane (0:100 to 5:95) to give 3.77 g of the diastereomeric mixture. Material was purified on a Chiralpak® AD column eluting with ethanol (0.2% dimethethylamine):acetonitrile (0:100 to 100:0) to obtain the title compound as white solid (1.7 g, 3.7 mmol, 37%). MS (m/z): 465 (M+1).

PREPARATION 13

Methyl 2-(2-bromophenyl)acetate

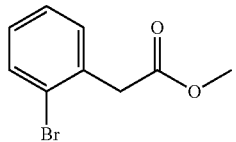

Combine 2-bromophenylacetic acid (500.0 g, 2.33 mol) with methanol (5.0 L) under a nitrogen atmosphere. Add concentrated sulfuric acid (185.8 mL) drop-wise at 20-35° C., and then warm to 60-65° C. with stirring for 3-4 hours. Cool the reaction mixture to 45° C. and concentrate under reduced pressure below 45° C. to a volume of approximately 750 mL. Cool the reaction mixture to 10-30° C. and add dichloromethane (2.5 L). Adjust the pH to 7-8 with sodium hydroxide (7%, 380.0 mL) and separate the layers. Concentrate the organic phase to dryness under reduced pressure below 45° C. to obtain the title compound (516.5 g, 97.0%) as a yellow oil.

PREPARATION 14

5,7-Dihydropyrido[2,3-d][3]benzazepin-6-one

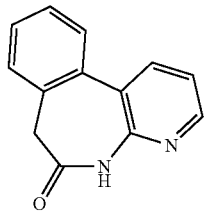 [SMILES: O=C1Cc2ccccc2-c2cccnc2N1]

Combine methyl 2-(2-bromophenyl)acetate (1.0 kg, 4.36 mol), dioxane (11.0 L), and N-methyl-2-pyrrolidone (7.0 L) with stirring at room temperature. Add bis(pinacolato)diboron (1.2 kg, 4.58 mol) and potassium acetate (855.9 g, 8.72 mol) to the mixture, and then degas the solution by passing nitrogen gas through the solution for 2-3 hours. Charge [1,1'-bis(diphenylphosphino)ferrocene]palladium(II) dichloride dichloromethane adduct (71.2 g, 97.2 mmol) under an atmosphere of nitrogen and then heat the reaction mixture to 80-90° C. for 18-20 hours to obtain methyl 2-[2-(4,4,5,5-tetramethyl-1,3,2-dioxaborolan-2-yl)phenyl]acetate as a solution which is used without isolation. Cool the reaction mixture to 15-25° C. and add 2-amino-3-bromopyridine (675.0 g, 3.90 mol) and a solution of potassium phosphate tribasic (2.41 kg, 11.3 mol) in water (3.0 L). Degas the solution by passing nitrogen gas through the solution for 2-3 hours, and add [1,1'-bis(diphenylphosphino)ferrocene]palladium(II) dichloride dichloromethane adduct (106.8 g, 130.8 mmol), then heat the reaction mixture to 80-90° C. for 18-40 hours. Cool the reaction mixture to 50-60° C., and slowly add a solution consisting of saturated sodium bicarbonate (13.0 L), saturated sodium chloride (13.0 L), and water (13.0 L). Stir the mixture for 2-3 hours at 50-60° C., cool to 15-25° C. and stir for an additional 18-20 hours. Filter the resulting solids and wash the filter cake with water (2×2.0 L). Transfer the solids to a clean reaction vessel, add ethyl acetate (5.0 L), and heat the mixture to 60-70° C. for 2-3 hours. Cool the solution to 15-25° C. and stir it for 1-2 hours and filter the resulting solids. Wash the filter cake with ethyl acetate (2×750 mL) and dry the resulting solids under vacuum to provide the title compound (644.0 g, 68.1%) as an off-white solid.

PREPARATION 15

5-[2-(tert-Butyl(dimethyl)silyl)oxyethyl]-7H-pyrido[2,3-d][3]benzazepin-6-one

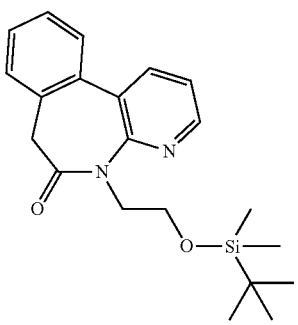 [SMILES: CC(C)(C)[Si](C)(C)OCCN1C(=O)Cc2ccccc2-c2cccnc21]

Add 5,7-dihydropyrido[2,3-d][3]benzazepin-6-one (33.8 g, 0.16 mol) in acetonitrile (340.0 mL) and stir at 20-30° C. for 0.5-1 hour. Add cesium carbonate (104.6 g, 0.32 mol) and (2-bromoethoxy)-tert-butyldimethylsilane (42.2 g, 0.18 mol) and heat the reaction mixture to 70-80° C. for 18-20 hours. Cool the reaction mixture to 20-25° C. and filter through diatomaceous earth (50.6 g). Wash the filter cake with acetonitrile (2×50.6 mL) and concentrate the filtrate under reduced pressure to arrive at a total volume of approximately 67.5 mL. Add toluene (152 mL), active carbon (2.53 g) and heat the mixture to 60-70° C. for 1-2 hours. Cool the mixture to 25-35° C. and filter the reaction mixture over diatomaceous earth (50.6 g). Rinse the filter cake with toluene (17.0 mL) and concentrate under reduced pressure to obtain the title compound as a light brown oil that crystallizes on standing (56.8 g, 92.2%).

PREPARATION 16

5-[2-(tert-Butyl(dimethyl)silyl)oxyethyl]-7-hydroxy-imino-pyrido[2,3-d][3]benzazepin-6-one

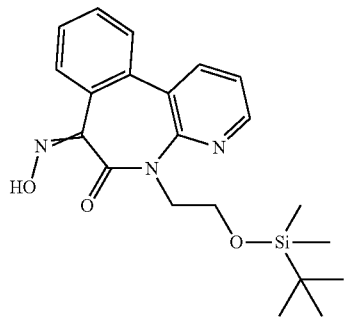 [SMILES: CC(C)(C)[Si](C)(C)OCCn1c(=O)c(=NO)c2ccccc2c2cccnc21]

Combine 5-[2-(tert-butyl(dimethyl)silyl)oxyethyl]-7H-pyrido[2,3-d][3]benzazepin-6-one (30.0 g, 0.08 mol) and toluene (300.0 mL), cool the reaction mixture to −10-0° C. Add potassium tert-butoxide (18.2 g, 0.16 mol), isoamyl nitrite (13.34 g, 0.11 mol) and then stir for 3-5 hours. Transfer the reaction mixture to a cool (0-5° C.) biphasic solution of ethyl acetate (210 mL) and water (510 mL) and stir for 15-30 minutes. Warm the reaction mixture to 15-25° C. and separate the layers. Extract the aqueous layer with additional ethyl acetate (120 mL) and methyl tert-butyl ether (120 mL) and combine the organic layers. Concentrate the organic under reduced pressure to a solution volume of approximately 60-90 mL and then add toluene (240 mL) and ethyl acetate (75 mL). Filter the solution through silica gel (45.0 g), rinse the silica gel with a mixture of toluene (210 mL) and ethyl acetate (60 mL), and concentrate the filtrate under reduced pressure to a volume of approximately 75 mL. Add heptane (120 mL) and concentrate the mixture to a volume of approximately 60 mL and filter the resulting solids. Wash the filter cake with heptane (25 mL) and dry under vacuum to provide the title compound (28.3 g, 72.5%) as a yellow solid.

PREPARATION 17

7-Amino-5-[2-(tert-butyl(dimethyl)silyl)oxyethyl]-7H-pyrido[2,3-d][3]benzazepin-6-one

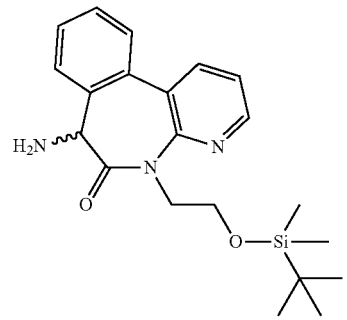 [SMILES: CC(C)(C)[Si](C)(C)OCCN1C(=O)C(N)c2ccccc2-c2cccnc21]

Combine 5-[2-(tert-butyl(dimethyl)silyl)oxyethyl]-7-hydroxyimino-pyrido[2,3-d][3]benzazepin-6-one (206.0 g, 0.52 mol) and tetrahydrofuran (2.3 L) into an autoclave under an atmosphere of nitrogen. Add Raney nickel (232.0 g, 1.13 wt/wt equivalents) to the reaction mixture and introduce hydrogen atmosphere (87 psi). Stir the reaction mixture at 60-65° C. for 24 hours. Filter the mixture over diatomaceous earth and wash the filter aid with tetrahydrofuran (500 mL). Concentrate the filtrate to obtain the title compound (196.0 g, 93.2%) as a brown oil. MS (m/z): 384 (M+1).

PREPARATION 18 tert-Butyl N-[(1S)-2-[[5-(2-hydroxyethyl)-6-oxo-7H-pyrido[2,3-d][3]benzazepin-7-yl]amino]-1-methyl-2-oxo-ethyl]carbamate Chiral

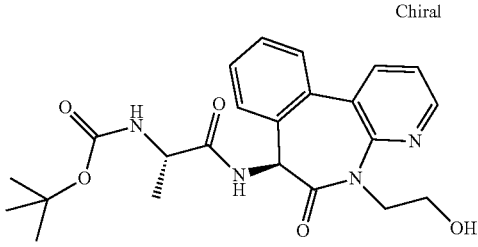 [SMILES: C[C@H](NC(=O)OC(C)(C)C)C(=O)N[C@@H]1C(=O)N(CCO)c2ncccc2-c2ccccc21]

Combine 7-amino-5-[2-(tert-butyl(dimethyl)silyl)oxyethyl]-7H-pyrido[2,3-d][3]benzazepin-6-one (166.0 g, 0.43 mol), dichloromethane (2.2 L), and L-Boc-alanine (106.4 g, 0.56 mol) under nitrogen atmosphere. Add hydroxybenzotriazole (1.46 g, 10.8 mmol) and triethylamine (102.5 mL, 0.74 mol) maintaining the internal temperature below 30° C. Add 1-ethyl-3-(3-dimethylaminopropyl)carbodiimide (128.2 g, 0.67 mol) in portions and stir for 16-18 hours at 20-30° C. Purify the reaction mixture by silica gel chromatography (300 g silica gel), eluting with dichloromethane (498 mL×2). Combine the dichloromethane solution and wash it with water (2×3.3 L). Concentrate the organic phase under reduced pressure to a volume of 300 mL to 400 mL and add ethyl acetate (664.0 mL). Concentrate the mixture under reduced pressure to a volume of 300-400 mL, and add ethyl acetate (664 mL). Concentrate the mixture under reduced pressure to a volume of 300-400 mL, and add ethyl acetate (1.3 L). Add tetra-n-butylammonium fluoride trihydrate (149.4 g, 0.47 mol) and stir for 16-18 hours at 20-30° C. Add an aqueous solution of sodium chloride (20%, 1.6 L), separate the layers, and wash the organic phase again with aqueous sodium chloride (20%, 1.6 L). Concentrate the organic to an approximate volume of 800-900 mL and stir the mixture for 12-16 hours at 20-30° C. Filter the resulting solids, wash the filter cake with ethyl acetate (91.3 mL). Purify the filtrate with silica gel chromatography (300 g silica gel), eluting with ethyl acetate (2×500 mL) to provide the title compound (82.6 g, 85.2% de, 100% ee, 51.2% yield) as a yellow oil. MS (m/z): 441 (M+1).

PREPARATION 19

(2S)-2-Amino-N-[(7S)-5-(2-hydroxyethyl)-6-oxo-7H-pyrido[2,3-d][3]benzazepin-7-yl]propanamide

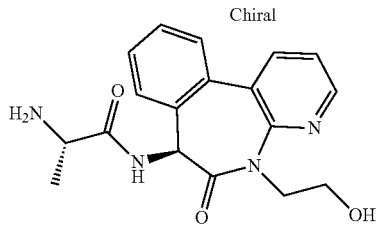 [SMILES: C[C@H](N)C(=O)N[C@@H]1C(=O)N(CCO)c2ncccc2-c2ccccc21]

Combine tert-butyl N-[(1S)-2-[[5-(2-hydroxyethyl)-6-oxo-7H-pyrido[2,3-d][3]benzazepin-7-yl]amino]-1-methyl-2-oxo-ethyl]carbamate (54.0 g, 0.12 mol) and acetonitrile (212.7 mL) under a nitrogen atmosphere. Add hydrochloric acid (317.5 mL, 4N, 1.27 mol) drop-wise to maintain the internal temperature below 30° C., and stir the reaction mixture for 16-18 hours at 20-30° C. Add water (324.0 mL) and dichloromethane (430 mL) and separate the layers. Discard the organic layer and to the aqueous phase add dichloromethane (645 mL) and adjust the pH to approximately 10 using aqueous sodium hydroxide (20%, 252 mL). Separate the layers, extract the aqueous layer with additional dichloromethane (2×430 mL), and combine the organic phases. Concentrate the organic under reduced pressure below 45° C. to an approximate volume of 130-150 mL, and add tetrahydrofuran (322 mL). Concentrate the solution under reduced pressure below 45° C. to an approximate volume of 200-220 mL, and add additional tetrahydrofuran (213 mL). Concentrate the reaction mixture under reduced pressure to an approximate volume of 250-270 mL, and heat to 60-65° C. for 2-3 hours. Cool the reaction mixture to 5-15° C. slowly and stir for 5-8 hours. Filter the resulting solids, wash the filter cake with ethyl acetate (56 mL). Transfer the solids to a clean reaction vessel, add ethyl acetate (150 mL), and heat to 60-65° C. for 2-3 hours, then cool the solution to 5-15° C. slowly. Stir for 2-3 hours at this temperature and collect the resulted solids by filtration. Wash the filter cake with ethyl acetate (45 mL) and dry the solids in an oven under reduced pressure below 60° C. to provide the title compound (21.0 g, 99.2% de, 100% ee, 51.0% yield) as an off white solid. MS (m/z): 341 (M+1).

EXAMPLE 2

4,4,4-Trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide Hydrate

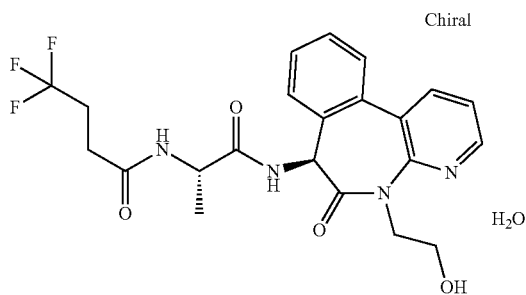 [SMILES: C[C@H](NC(=O)CCC(F)(F)F)C(=O)N[C@@H]1C(=O)N(CCO)c2ncccc2-c2ccccc21 ; O]

Combine (2S)-2-amino-N-[(7S)-5-(2-hydroxyethyl)-6-oxo-7H-pyrido[2,3-d][3]benzazepin-7-yl]propanamide (45.0 g, 132.2 mmol) and dimethylformamide (452.9 mL) under a nitrogen atmosphere. Cool to 0-5° C. and add N-ethyldiisopropylamine (77.4 mL, 444.0 mmol), 4,4,4-trifluorobutyric acid (19.9 g, 139.3 mmol), and hydroxybenzotriazole monohydrate (22.3 g, 153.1 mmol). Stir the solution for 5-10 min and add 1-ethyl-3-(3-dimethylaminopropyl)carbodiimide hydrochloride (30.6 g, 159.6 mmol) in one portion. Warm the reaction mixture to 20-25° C. and stir for 1-2 hour. Add ethyl acetate (1.4 L) and water (1.8 L) and stir for 0.5-1 hour. Separate the phases and wash the organic layer with an aqueous sodium bicarbonate solution (5%, 1.0 L) and concentrate the solution under reduced pressure to obtain a volume of 200-300 mL. Add ethanol (522 mL) and concentrate the solution under reduced pressure to obtain a volume of 200-300 mL. Repeat for three times. Add ethanol (180 mL) and 5% solution of potassium carbonate (34.6 mL) and stir for 0.5-1 hour at 20-25° C. Add water (667 mL) and seed crystals of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate (0.4 g, 0.86 mmol) (Seed crystals can be generated from the solids obtained from previous lots of the product, or can be obtained using other methods common known and used by one skilled in the art, such as recrystallization of a small aliquot) and stir for 2-3 hours at 20-25° C. Filter and wash the filter cake with a mixture of ethanol (63 mL) and water (42 mL) twice. Dry the resulting solids in an oven under reduced pressure below 40° C. to provide the title compound (41.9 g, 99.6% de, 100% ee, 65.3% yield) as a white to off white solid. MS (m/z): 465 (M-H$_2$O+1).

XRPD of Example 2

The XRPD patterns of crystalline solids are obtained on a Bruker D4 Endeavor X-ray powder diffractometer, equipped with a CuKα source (λ=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. (For example, see: U. S. Pharmacopia 33—National Formulary 28 Chapter <941> Characterization of Crystalline Solids by X-ray Powder Diffraction (XRPD) Official Oct. 1, 2010-Feb. 1, 2011). Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction pattern is collected at ambient temperature (19-25° C.) and relative humidity (20-60%).

Thus, a prepared sample of the compound of Example 2 is characterized by an XRPD pattern using CuKα radiation as having diffraction peaks (2-theta values) as described in Table 1 below. The form is crystalline and contains a peak at 22.97 degree in combination with one or more of the peaks selected from the group consisting of 11.96, 18.81, 20.78, and 21.07 degrees 2-theta, with a tolerance for the diffraction angles of 0.2 degrees.

TABLE 1

X-ray powder diffraction peaks of Example 2:

| Peak | Angle (2-Theta °) | Intensity % |
|---|---|---|
| 1 | 7.573 | 0.8 |
| 2 | 9.177 | 2.3 |
| 3 | 11.96 | 50.4 |
| 4 | 13.063 | 24.6 |
| 5 | 14.036 | 21.5 |
| 6 | 14.352 | 2.9 |
| 7 | 15.223 | 32.4 |
| 8 | 16.845 | 15.8 |
| 9 | 17.12 | 11.8 |
| 10 | 17.828 | 23.4 |
| 11 | 18.481 | 10.6 |
| 12 | 18.809 | 25.3 |
| 13 | 19.396 | 11.7 |
| 14 | 20.102 | 28 |
| 15 | 20.778 | 44.2 |
| 16 | 21.068 | 63.8 |
| 17 | 22.713 | 36.8 |
| 18 | 22.967 | 100 |
| 19 | 23.407 | 7.4 |
| 20 | 23.625 | 2.4 |
| 21 | 24.11 | 5.3 |
| 22 | 24.772 | 49 |
| 23 | 25.028 | 6.5 |
| 24 | 25.311 | 11.5 |
| 25 | 25.868 | 1.8 |
| 26 | 26.586 | 14.6 |
| 27 | 27.979 | 25.6 |
| 28 | 28.27 | 6.6 |
| 29 | 29.033 | 3.6 |
| 30 | 29.54 | 14.3 |
| 31 | 29.9 | 12.2 |
| 32 | 30.556 | 9.9 |
| 33 | 30.766 | 11.5 |
| 34 | 31.703 | 1.3 |
| 35 | 32.186 | 10.1 |
| 36 | 33.015 | 1.4 |
| 37 | 33.822 | 3.4 |

TABLE 1-continued

X-ray powder diffraction peaks of Example 2:

| Peak | Angle (2-Theta °) | Intensity % |
|---|---|---|
| 38 | 34.007 | 2 |
| 39 | 34.451 | 1.1 |
| 40 | 34.728 | 0.5 |
| 41 | 35.381 | 2.7 |
| 42 | 35.601 | 5.8 |
| 43 | 36.052 | 3.2 |
| 44 | 36.272 | 3.5 |
| 45 | 36.866 | 7.2 |
| 46 | 37.73 | 0.8 |
| 47 | 38.232 | 0.2 |
| 48 | 38.608 | 1.2 |
| 49 | 39.139 | 1.5 |

Solid State NMR of Example 2

$^{13}$C Cross polarization/magic angle spinning (CP/MAS) NMR (solid-state NMR or SSNMR) spectra are obtained using a Bruker Avance II 400 MHz NMR spectrometer (Lilly tag K299547) operating at a carbon frequency of 100.622 MHz and equipped with a Bruker 4 mm triple resonance probe (K299551). TOSS sideband suppression is used along with cross polarization employing SPINAL64 decoupling (70.8 Watts) and a RAMP100 shaped H-nucleus CP pulse. Acquisition parameters are as follows: 90° proton r.f. pulse width of 2.5 µs, contact time was 3.5 ms, pulse repetition time of 5 s, MAS frequency of 10 kHz, spectral width of 30 kHz, acquisition time is 34 ms and the number of scans is 10,587. Chemical shifts are referenced to adamantane (δ=29.5 ppm) in a separate experiment. $^{13}$C NMR (solid-state): δ (ppm) 18.65, 27.52, 28.76, 47.66, 49.96, 55.02, 58.88, 122.87, 126.49, 129.73, 131.37, 132.31, 137.28, 145.01, 149.17, 168.53, 170.30, 175.55.

Karl Fischer Titration of Example 2

Karl Fischer titrations are obtained using a Brinkmann Methrohm 756 KF Coulometer. The control standard is determined using Hydranol® as a water standard in duplicate. Run the sample in triplicate and record the average percentage of water to determine the amount of water in a sample. Karl Fischer Titration average result of Example 2 is 3.9% water. Theoretic percentage of one molar equivalent of water in Example 2 is 3.7%.

Cancer is increasingly recognized as a heterogeneous collection of diseases whose initiation and progression are induced by the aberrant function of one or more genes that regulate DNA repair, genome stability, cell proliferation, cell death, adhesion, angiogenesis, invasion, and metastasis in cell and tissue microenviroments. Variant or aberrant function of the "cancer" genes may result from naturally occurring DNA polymorphism, changes in genome copy number (through amplification, deletion, chromosome loss, or duplication), changes in gene and chromosome structure (through chromosomal translocation, inversion, or other rearrangement that leads to deregulated gene expression), and point mutations. Cancerous neoplasms may be induced by one aberrant gene function, and maintained by the same aberrant gene function, or maintenance and progression exacerbated by additional aberrant gene functions.

Beyond the genetic chromosomal aberrations mentioned above, each of the cancers may also include epigenetic modifications of the genome including DNA methylation, genomic imprinting, and histone modification by acetylation, methylation, or phosphorylation. An epigenetic modification may play a role in the induction and/or maintenance of the malignancy.

Diagnosis of cancerous malignancies by biopsy, immunophenotyping and other tests are known and routinely used. In addition to high resolution chromosome banding and advanced chromosomal imaging technologies, chromosome aberrations in suspected cases of cancer can be determined through cytogenetic analysis such as fluorescence in situ hybridization (FISH), karyotyping, spectral karyotyping (SKY), multiplex FISH (M-FISH), comparative genomic hybridization (CGH), single nucleotide polymorphism arrays (SNP Chips) and other diagnostic and analysis tests known and used by those skilled in the art.

PET/CT imaging of cancer with combined positron emission tomography (PET) and X-ray computerized tomography (CT) scanners has become a standard component of diagnosis and staging in oncology. The use of the radiolabeled tracer 2-deoxy-2-[$^{18}$F]fluoro-D-glucose (FDG) is used for the majority of all PET/CT imaging procedures. One of the advantages of PET/CT imaging is its ability to detect, very early during treatment, significant changes in glucose metabolism or even complete shutoff of the neoplastic cell metabolism as a surrogate of tumor chemosensitivity assessment. In addition to cancer detection and staging, PET/CT imaging is becoming increasingly important as a quantitative monitor of individual response to therapy and an evaluation tool for new drug therapies. Changes in FDG accumulation have been shown to be useful as an imaging marker for assessing response to therapy. RECIST criteria, where response of tumors to therapy has traditionally assessed by measurement of changes in size/dimension of the tumors in CT images may not evidence early response to the therapy. Changes in size of tumors as a result of therapy may take a long period of time to develop. The most widely used parameter is the standardized uptake value (SUV) is defined as the maximal SUV value ($SUV_{MAX}$) in the region of interest and reduction in $SUV_{MAX}$ is generally considered the most reliable indicator of the metabolic activity shutdown.

The oncogenic role of Notch was first reported in human T-cell leukemia involving a translocation of the Notch1 intracellular domain to the T-cell receptor-β promoter region, resulting in the over expression of Notch1 intracellular domain (Grabher et al. *Nature Review Cancer,* 2006 (6):347-359; Weng et al. *Science,* 2004(306):269-271). Over expression of Notch1 intracellular domain in hematopoietic progenitor cells of mice caused the mice to exhibit T-cell acute lymphoblastic leukemia similar to humans. In addition to T-cell acute lymphoblastic leukemia, there is increasing evidence that Notch signals are oncogenic in other cancers through multiple mechanisms including acute lymphoblastic leukemia, acute myelogenous leukemia, chronic myelogenous leukemia and erythroleukemia. Aberrant constitutive Notch signaling is also implicated in a number of solid tumor malignancies including breast cancer, ovarian cancer (Park et al. *Cancer Research,* 2006(66):6312-6318), melanoma (Gast et al. *Genes. Chromosomes & Cancer,* 2010 (49):733-745), lung cancer, non-small cell lung cancer (Westhoff et al. *PNAS,* 2009(106):22293-22298), pancreatic cancer, glioblastoma, colorectal cancer, head and neck cancer, cervical cancer, prostate cancer, liver cancer, squamous cell carcinoma (oral), skin cancer and medulloblastoma (Ranganathan et al., *Nature Review Cancer,* 2011(11):338-351 and Supplementary Information S1 (table)). Aberrant Notch signaling may be activated in particular soft tissue sarcomas Guijarro et al. *Am J Pathol,* 2013 (182(6)):2015-2027. There are recent reports of Notch inhibitors being evaluated alone in phase 1 clinical studies in which leiomyosarcoma patients were enrolled, Pant et al. *J Clin Oncol,* 2012 (30(15)): May 20 Supplement, Abstract 3008; Messersmith et al. *Clin Cancer Res* (21(1)):60-67; and in combination with vismodegib, a Hedgehog antagonist, www.clinicaltrials.gov, Identifier: NCT01154452, downloaded 20 Dec. 2014. No complete response or partial response data are reported for LMS patients in Pant et al. or Messersmith et al. and no data have been found reported for the combination clinical study. Inhibition of Notch signaling presents an attractive target to provide therapeutic benefits to cancer patients whose disease was induced, maintained and progressed, or exacerbated by aberrant activation of constitutive Notch signaling pathway. Shih et al. *Cancer Research,* 2007(67)1879-1882.

Clinical Evaluation

A study of 4,4,4-Trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate in patients with advanced or metastatic cancer.

Study Design

This study is a multicenter, nonrandomized, open-label, dose-escalation study followed by cohort expansion of oral dosed 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate in outpatients with advanced or metastatic cancer.

Study Objectives

The primary objective of this study is to determine a recommended Phase 2 dose of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate that may be safely administered to patients with advanced or metastatic cancer.

The secondary objectives of the study are to characterize the safety and toxicity profile of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate as assessed by National Cancer Institute's (NCI) Common Terminology Criteria for Adverse Events (CT-CAE) v4.0; to estimate the pharmacokinetic (PK) parameters of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate; and to document any antitumor activity observed with 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate.

Exploratory objectives are to explore renal clearance and PK metabolites of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate in plasma and urine; explore predictive biomarkers related to 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate; explore pharmacodynamic (PD) effects of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate on biomarkers indicative of Notch activity (Notch intracellular domain by immunohistochemistry or an alternative validated method) including cytokeratin 18 or Rules Based Medicine; and explore the utility of positron emission tomography (PET) scan or PET/CT to assess treatment effect with 4,4,4- trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate.

Trial Drug 4,4,4-Trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate, dose range 2.5 to 100 mg, given orally as capsules 3 times per week during a 28-day cycle.

4,4,4-Trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate will be supplied as capsules in bottles for oral consumption. These capsules should be stored at room temperature within the temperature range stated on the label.

Planned Duration of Treatment

Patients will receive 2 cycles (28 days each) of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate unless one or more of the criteria for discontinuation are fulfilled. A patient may receive more than 2 cycles of treatment only if: 1) none of the criteria for discontinuation have been fulfilled, and 2) the investigator determines that the patient is experiencing clinical benefit from the treatment.

A short-term follow-up period (post-discontinuation) of 30 days is planned.

Dosing 4,4,4-Trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate will be administered orally TIW during both the dose-escalation phase (Part A) and the dose-confirmation phase (Part B).

Criteria for Evaluation

Safety: NCI CTCAE, version 4.0, dose-limiting toxicities (DLT).

nance imaging (MRI); chest X-ray; PET scan; PET/CT imaging Standardized Uptake Values ($SUV_{MAX}$).

Statistical Methods

Safety: Dose escalation will be driven by safety using the 3+3 method. Model-based analyses that incorporate prior expectations about the dose-toxicity curve will be fitted to the data at the end of each cohort, which will be used by investigators and Lilly clinical research physician to determine the next dose level. The maximum tolerated dose is defined as the highest tested dose that has less than 33% probability of causing a DLT during Cycle 1.

Efficacy:

Tumor response data will be tabulated and summarized by study part.

Pharmacokinetics:

PK parameters for 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate will be analyzed by standard non-compartmental methods of analysis.

Pharmacodynamics:

All PD data will be assessed. Exploratory PK/PD analyses may be conducted to identify the exposure-biomarker response relationship.

Data on 3 patients having leiomyosarcoma administered 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate in cycle 1 of an ongoing clinical trial are presented in Table 2. Patient 1 was previously treated for leiomyosarcoma with surgery, radiation therapy and 5 prior regimens of systemic therapeutic or targeted therapies. Patient 2 was previously treated for leiomyosarcoma with surgery, radiation therapy, brachytherapy and 3 prior regimens of systemic therapeutic or targeted therapies. Patient 3 was previously treated for leiomyosarcoma with surgery and 3 prior regimens of systemic therapeutic or targeted therapies.

TABLE 2

| Initial Oral Drug Dose (mg) T.I.W. | Patient | Treatment Cycle | Study Day of CT Scan Assessment | CT Scan findings | Overall Response DCE-US | Target Response |
|---|---|---|---|---|---|---|
| 100 | 1[fn] | 1 | 4 | Central portion of the tumor became hypodense | Confirmed | 90% necrosis |
| 75 | 2 | 1 | 2 (48 hrs after one dose. | Central portion of the tumor became hypodense | Confirmed | 80% necrosis |
| 75 | 3 | 1 | 2 | No significant change | Not confirmed | 20% necrosis |

DCE-US is Dynamic Contrast-Enhanced Ultrasonagraphy.
[fn]Patient 1 only received two doses at 100 mg and further dosing was at 50 mg then 25 mg. Patient 1 subsequently died of hepatic complications while still enrolled in the clinical evaluation and receiving additional cycles of trial drug.

Bioanalytical (including PK and PD): Plasma concentrations of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate.

Efficacy: Depending on the histology, efficacy will be assessed using Response Evaluation Criteria in Solid Tumors (RECIST) v1.1 for solid tumors, the Revised Criteria for Malignant Lymphoma, the Guidelines from the National Cancer Institute Working Group for CLL, or the Response Assessment in Neuro-Oncology (RANO) criteria for glioblastoma. Each patient will be assessed by 1 or more of the following radiologic tests for tumor measurement: X-ray computerized tomography (CT) scan; magnetic reso- In both patients 1 and 2, CT scan of the liver performed in the first week of treatment showed the central portion of the tumor became hypodense suggesting necrosis. This suggested necrosis was confirmed by DCE-US. The above preliminary data on patients having leiomyosarcoma reveals both patients demonstrated surprising and unexpected significant necrosis of their leiomyosarcoma tumor. In patient 3, there was no significant change observed from the initial scan.

After 1 cycle (28 days), additional CT scan imaging confirmed necrosis in all three patients.

Data on 19 additional patients having leiomyosarcoma administered 4,4,4-trifluoro-N-[(1S)-2-[[(7S)-5-(2-hydroxyethyl)-6-oxo-7H-pyrido[2,3-d][3]benzazepin-7-yl]

amino]-1-methyl-2-oxo-ethyl]butanamide hydrate in Part B of an ongoing clinical trial are presented in Table 3. Choi Response Criteria, were recorded for a limited number of patients and are not reported in Table 3, Choi et al, *J Clin Oncol.* 2007; 25:1753-1759.

TABLE 3

| Patient | First Assigned Dose | Best RECIST Response | Best Change in Tumor Size (%) | PET/CT Scan (change in SUVmax %) |
|---|---|---|---|---|
| 4 | 75 mg | PD | 23 | 58 |
| 5 | 75 mg | SD | 2 | 10 |
| 6 | 75 mg | Unconfirmed PR | Unknown (data query outstanding) | 32 |
| 7 | 75 mg | SD | 13 | −4 |
| 8 | 50 mg | PD | 13 | −7 |
| 9 | 50 mg | PD | 60 | |
| 10 | 50 mg | PD | 37 | 37 |
| 11 | 50 mg | SD | 19 | −5 |
| 12 | 50 mg | PD | 20 | −30 |
| 13 | 50 mg | Not Done | Data not available | |
| 14 | 50 mg | SD | −13 | 0 |
| 15 | 50 mg | PD | 33 | |
| 16 | 50 mg | PD | 24 | −11 |
| 17 | 50 mg | PD | Data not available | |
| 18 | 50 mg | PD | 23 | |
| 19 | 50 mg | Not Done | Data not available | |
| 20 | 50 mg | SD | Data not available | 16 |
| 21 | 50 mg | PD | 50 | |
| 22 | 50 mg | SD | Data not available | |

The above data on patients having leiomyosarcoma, particularly the PET/CT $SUV_{MAX}$, data shows a beneficial clinical effect in leiomyosarcoma tumor patients.

We claim:

1. A method of treating a patient suffering from leiomyosarcoma, the method comprising:
   administering to a patient determined to have advanced or metastatic leiomyosarcoma an effective amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide or a pharmaceutically acceptable salt or hydrate thereof.

2. The method of claim 1, wherein 2.5 to 100 mg/patient/day of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide or a pharmaceutically acceptable salt or hydrate thereof is administered.

3. The method of claim 2, wherein 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide or a pharmaceutically acceptable salt or hydrate thereof is administered every other day over a five day period followed by two days without administration (T.I.W.).

4. The method of claim 3, wherein 10 to 75 mg/patient/day of 4,4,4-trifluoro-N-[(1 S)-2-[[(7 S)-5-(2-hydroxyethyl)-6-oxo-7H-pyrido[2,3-d][3]benzazepin-7-yl]amino]-1-methyl-2-oxo-ethyl]butanamide or a pharmaceutically acceptable salt or hydrate thereof is administered.

5. The method of claim 4, wherein 25 to 75 mg/patient/day of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide or a pharmaceutically acceptable salt or hydrate thereof is administered.

6. The method of claim 1, wherein the administering is oral.

7. The method of claim 6, wherein 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide or a pharmaceutically acceptable salt or hydrate thereof is formulated in a capsule.

8. The method of claim 1, wherein the patient has been previously treated for the leiomyosarcoma with surgery.

9. The method of claim 2, wherein 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide or a pharmaceutically acceptable salt or hydrate thereof is administered three times per week.

* * * * *